United States Patent [19]

Brackenridge et al.

[11] Patent Number: 4,717,776

[45] Date of Patent: Jan. 5, 1988

[54] BROMINATION PROCESS

[75] Inventors: David R. Brackenridge; Bonnie G. McKinnie, both of Baton Rouge, La.

[73] Assignee: Ethyl Corporation, Richmond, Va.

[21] Appl. No.: 854,015

[22] Filed: Apr. 21, 1986

[51] Int. Cl.[4] ...................... C07C 43/225; C07C 41/22
[52] U.S. Cl. ...................................... 568/637; 568/639
[58] Field of Search ................................ 568/637, 639

[56] References Cited

U.S. PATENT DOCUMENTS 3,752,856  8/1973  Nagy et al. ........................ 568/639

*Primary Examiner*—Werren B. Lone
*Attorney, Agent, or Firm*—Donald L. Johnson; John F. Sieberth; Joseph D. Odenweller

[57] ABSTRACT

A process for partially brominating polyphenylene ether (e.g. diphenly ether) in the absence of a solvent by adding the polyphenylene ether to a stoichiometric excess of liquid bromine containing a zirconium halide catalyst.

17 Claims, No Drawings

BROMINATION PROCESS

BACKGROUND OF THE INVENTION

Procedures for making perbrominated polyphenylene ethers are known. For example, decabromodiphenyl ether (referred to as "Decabrom") is a commercial fire retardant. It can be made by adding molten diphenyl ether to a large stoichiometric excess of liquid bromine containing a halogenation catalyst such as aluminum halide (U.S. Pat. No. 3,965,197). Although it is not a solvent, the large excess of bromine acts as a liquid medium in which the product is suspended and from which it can be readily recovered.

In some uses it is preferred to have only a partially brominated flame retardant because it might have more desirable physical properties in a particular substrate. For example a partially brominated diphenyl ether is sold as octabromodiphenyl ether (referred to at "Octabrom") although its actual composition is a mixture of partially brominated dipheny ether. The commercial grade product contains about 6–9 bromine atoms per molecule.

Using the aluminum halide bromination catalyst as practiced in U.S. Pat. No. 3,965,197, the degree of bromination can only be limited by restricting the amount of bromine to about the stoichiometric amount required to insert eight bromine atoms per molecule. Also the product is very colored (yellow to brown) requiring extensive purification if a light colored product is required.

SUMMARY OF THE INVENTION

It has now been discovered that a polyphenylene ether such as diphenyl ether can be partially brominated to contain about 3–4 bromine atoms per benzene ring by conducting the reaction in a large stoichiometric excess of liquid bromine and using a zirconium halide catalyst which may be promoted with a small amount of iron. The product is much lighter colored than that obtained by adding a stoichiometric amount of bromine to diphenyl ether.

DESCRIPTION OF THE PREFERRED EMBODIMENTS

A preferred embodiment of the invention is a process for making a partially brominated polyphenylene ether, said process comprising reacting said polyphenylene ether with bromine in the presence of a zirconium halide catalyst, at a temperature from about 10° C. up to reflux.

Polyphenylene ethers as used herein means a compound having two or more benzene rings connected through an oxygen atom. They can be represented by the formula

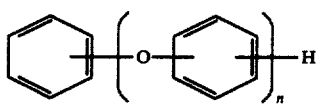

wherein n is an integer having a value of at least 1 up to 20 or more. Some examples of these are: diphenyl ether, 1,4-diphenoxybenzene, 1,3-diphenoxybenzene, 1,2-diphenoxybenzene, tetra-(p-phenyleneoxy)benzene wherein "tetra-(p-phenyleneoxy)" means four of the above

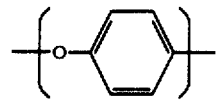

groups bonded in the para position, i.e.

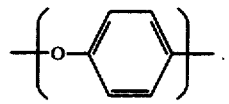

The most important polyphenylene ethers are diphenyl ether and the various isomers of diphenoxybenzene, especially 1,4-diphenoxybenzene.

The amount of bromine used is an amount in excess of the stoichiometric amount required to substitute four bromine atoms per benzene ring. For example with diphenyl ether the stoichiometric amount is 8 moles of bromine per mole of diphenyl ether. With diphenoxybenzene the stoichiometric amount is 12 moles of bromine per mole of diphenoxybenzene.

The stoichiometric excess can range from about 25% up to 500% or more. This means that the amount of bromine ranges from about 5 to 24 moles, more preferably 6 to 24 moles per equivalent of polyphenylene ether wherein an equivalent of polyphenylene ether is the molecular weight divided by the number of benzene rings per molecule. Thus with diphenoxybenzene the amount of bromine can range from about 15–72 moles, more preferably 18–72 moles per mole of diphenoxybenzene. With diphenyl ether the amount of bromine can range from about 10 to 48 moles, more preferably 12 to 48 moles of bromine per mole of diphenyl ether.

The excess bromine acts as a liquid reaction medium in which the bromination is conducted. No other solvent is required and it is preferred that no other solvent be used since such use can contaminate the product.

The critical feature of the invention is the use of a zirconium halide catalyst rather than the conventional aluminum halide catalyst which cause perbromination. When aluminum halides are used a partially brominated product will not result when using an excess amount of bromine. With aluminum halides the amount of bromine must be restricted to close to the stoichiometric amount.

Any zirconium halide can be used such as zirconium chloride, zirconium bromide, zirconium fluoride and mixtures thereof. The most readily available zirconium halide is zirconium tetrachloride. In the reaction mixture the catalytic species is very likely zirconium tetrabromide since large amounts of hydrogen bromide are evolved which can convert any of the zirconium tetrahalides to zirconium tetrabromide.

The amount of zirconium halide should be an amount which will catalyze the reaction of bromine with the polyphenylene ether to substitute bromine into the benzene rings. A useful range in which to operate is about 0.1–10 weight percent based on the amount of bromine. A more preferred range is about 0.3–5 weight percent based on the bromine charge.

The reaction is preferably conducted by charging the bromine and zirconium halide to a reaction vessel and then feeding the polyphenylene ether to the liquid bromine. The reaction temperature can range from below ambient (e.g. −10° C.) up to reflux temperature under reaction conditions. Although bromine refluxes at about 59° at atmospheric pressure, the reaction may be conducted at above atmospheric pressure, for example 5 to 25 psig, under which conditions reflux temperature will increase.

More preferably the reaction is started at the temperature of the charged bromine (e.g. 20°-30° C.) and is permitted to rise during the course of the reaction to a higher temperature (e.g. 30°-40° C.). Heat is then supplied to the reaction mixture to bring the mixture to reflux and speed up the reaction rate.

The polyphenylene ether may be added to the bromine as a solid or as a liquid. For ease of operation of the polyphenylene ether is preferably added molten even if this temperature is higher than the bromine temperature or even higher than bromine reflux temperature. For example, diphenyl ether melts at about 27° C. so it is typically fed to the bromine at about 28°-35° C. to prevent freeze up in the feed conduit.

The polyphenylene ether is added to the bromine over a period of time. Feed time depends on scale and ability to control temperature and handle hydrogen bromide evolution. On a laboratory scale the addition requires about 15 minutes to one hour. On a commercial scale, the reaction could take about 2-8 hours or longer.

After completion of the polyphenylene ether addition, the reaction mixture can be held for a period to assure the desired degree of bromination has been achieved. A ride period of about 4-5 hours at or near reflux is beneficial. When an iron promoter is used this time can be shortened.

Product can be recovered by any of several conventional methods. For example the reaction mixture can be mixed with water and the excess bromine distilled out. The product can then be recovered from the water by filtration or centrifugation and then dried and ground to the desired particle size. Alternatively, a solvent such as toluene can be added to the water-product mixture to dissolve the product. The solvent phase can be separated and the solvent distilled out leaving the product which is then crushed and ground to a fine powder.

The manner in which the above embodiment of the process can be conducted is shown in the following examples:

EXAMPLE 1

In a glass reaction vessel was placed 200 grams (1.25 moles, 56% stoichiometric excess based on diphenyl ether) of bromine and 1.7 grams of ZrCl$_4$. The vessel was fitted with a stirrer and reflux condenser which was vented through a mineral oil bubbler to a caustic scrubber to absorb evolved hydrogen bromide. Molten (28° C.) diphenyl ether (17 grams, 0.1 mole) was fed to the stirred bromine at 21°-22° C. over a 28 minute period. Heat was applied to increase the reaction temperature to reflux. Total reaction time was 4.13 hours and final temperature was 68.7° C. Water (120 ml) was then added to terminate the reaction. The excess bromine was distilled from the mixture to a pot temperature of about 100° C. Residual bromine was purged with nitrogen. Toluene (90 ml) was added to dissolve the product. Aqueous sodium sulfite (10 ml, 10 weight percent Na$_2$SO$_3$) was mixed with the toluene solution to remove trace bromine. The toluene layer separated, washed with 100 ml hot water and dried over magnesium sulfate. After filtration the toluene was removed under vacuum to a temperature of 130° C. at about 2 Torr. The product was cooled and crushed and analyzed by gas chromatography (area percent by GC) as follows:

| | |
|---|---|
| Hexabrom[1] | 27.8% |
| Heptabrom[1] | 50.3% |
| Octabrom[1] | 17.2% |
| Nonabrom[1] | 4.4% |
| Decabrom[1] | 0.4% |

[1]diphenyl ether.

A series of reactions was conducted following the above general procedure with minor variations as follows:

TABLE 1

| Example | ZrCl$_4$[2] | Bromine[3] | DPE[1] Addition Time (min.) | DPE[1] Addition Temp. (°C.) | Total Reaction Time (hrs.) | Final Reaction Temp. |
|---|---|---|---|---|---|---|
| 2 | 14.6 | 100 | 25 | 20–21 | 3.58 | 64.5 |
| 3 | 7.3 | 100 | 24 | 19–24 | 5.5 | 64.5 |
| 4 | 4.3 | 100 | 30 | 19–21 | 5.0 | 65.0 |
| 5 | 4.3 | 75 | 14 | 20–26 | 5.0 | 69.0 |
| 6 | 2.4 | 50 | 30 | 19–25 | 4.0 | 69.9 |

[1]Diphenyl ether
[2]Mole percent based on diphenyl ether
[3]Percent stoichiometric excess based on converting diphenyl ether to Octabrom

TABLE II

| | Product Analysis (Area percent by G.C.) | | | | |
|---|---|---|---|---|---|
| Example | Hexabrom | Heptabrom | Octabrom | Nonabrom | Decabrom |
| 2 | 10.4 | 49.2 | 24.1 | 13.3 | 3.0 |
| 3 | 4.9 | 38.6 | 30.7 | 21.3 | 4.5 |
| 4 | 4.2 | 32.6 | 35.7 | 21.1 | 6.3 |
| 5 | 6.2 | 35.0 | 37.9 | 18.2 | 2.7 |
| 6 | 16.5 | 45.0 | 28.2 | 9.0 | 1.3 |

As the above results demonstrate, the present process makes it possible to achieve partial bromination of a polyphenylene ether using a large stoichiometric excess of bromine as the only reaction medium.

In another embodiment of the invention the reaction rate is sharply increased while still controlling the degree of bromination to about 3-4 bromine atoms per benzene ring by conducting the process including a small promoter amount of iron. The iron is preferably added to the bromine in the form of iron particles such as iron powder. The amount of iron can range from about 0.01-1.0 gram atoms per gram moles of zirconium halide catalyst. A more preferred range is about 0.05-0.5 and still more preferably about 0.1-0.3 gram atoms of iron per mole of zirconium halide.

The following examples show the zirconium halide bromination process carried out with an iron promoter.

EXAMPLE 7

In a glass reaction vessel was placed 192.5 grams of bromine, 0.56 grams (0.0024 moles) zirconium chloride and 0.02 grams (0.00036 gram atoms) of iron powder. While stirring, 17 grams of molten diphenyl ether was added at 21°-27° C. over a 30 minute period. The reaction mixture was then heated to reflux (64° C.) and stirred until the amount of HBr evolved indicated that Octabrom had been formed. Total time from start of diphenyl ether feed was 3.2 hours.

The reaction was quenched with 150 ml of water and excess bromine was distilled out. A small amount (1.4 grams) of sodium sulfite in 50 ml water was added to decompose residual bromine. Then 100 ml of toluene was added to dissolve the product at about 85°-90° C. The organic layer was separated and washed with 150 ml of hot water and dried over magnesium sulfate. The mixture was filtered and the toluene distilled out under vacuum at 130°/1-2 Torr for 1 hour. The residual product (75.3 grams) analyzed by G.C. in area percent as follows:

| hexabrom | 6.21% |
|---|---|
| heptabrom | 48.9% |
| octabrom | 26.95% |
| nonabrom | 15.25% |
| decabrom | 2.69% |

Average bromine atoms per molecule was 7.59.

EXAMPLE 8

An experiment was conducted following the general procedure of Example 7 but using 575.4 grams of bromine (3.6 moles), 1.46 grams of zirconium tetrachloride (0.0063 moles), 0.07 grams of iron powder (0.00125 gram atoms) and 51.0 grams of diphenyl ether (0.3 moles). The molten diphenyl ether was added over a 1.35 hour period at 20°-25° C. followed by reflux. Total reaction time was 3.3 hours. Product recovery was the same as before. Yield 223.4 grams. G.C. analysis was as follows:

| hexabrom | 11.2% |
|---|---|
| heptabrom | 52.54% |
| octabrom | 24.19% |
| nonabrom | 10.6% |
| decabrom | 1.48% |

Average 7.39 bromine atoms per molecule. Melt range 72°-130° C.

As these results show, the use of an iron promoter with the zirconium halide catalyst gives about the same product distribution but achieves this in a much shorter time.

The partially brominated polyphenylene ethers are useful as flame retardants in a wide variety of organic materials such as polyethylene, polypropylene, polyesters, acrylonitrile-butadiene-styrene terpolymer, styrene, high impact polystyrene, styrene butadiene copolymer, styrene maleic anhydride copolymer, polyphenylene ethers and blends of the above. The amount used is generally an amount to provide about 5-15 weight percent bromine to the polymer. Synergists, such as antimony oxide, are routinely included.

We claim:

1. A process for making a partially brominated polyphenylene ether, said process comprising reacting said polypeneylene ether with bromine in the presence of a catalytic amount of a zirconium halide catalyst at a temperature from about 10° C. up to reflux wherein said process is conducted using about 5-24 moles of bromine for each equivalent weight of said polyphenylene ether wherein said equivalent weight is the molecular weight of the polyphenylene ether divided by the number of benzene rings in said polyphenylene ether.

2. A process of claim 1 conducted in the substantial absence of a solvent other than liquid bromine.

3. A process of claim 1 wherein said polyphenylene ether is a diphenoxybenzene.

4. A process fo claim 3 conducted using about 15-72 moles of bromine per mole of diphenoxybenzene.

5. A process of claim 1 wherein said polyphenylene ether is diphenyl ether.

6. A process of claim 5 conducted using about 10-48 moles of bromine per mole of diphenyl ether.

7. A process of claim 6 conducted by adding the diphenyl ether to the liquid bromine containing the zirconium halide catalyst.

8. A process of claim 7 wherein said zirconium halide is introduced into said bromine in the form of zirconium chloride.

9. A process for making brominated diphenyl ether which contains an average of about 6-8 bromine atoms per molecule, said process comprising adding about 1 mole of molten diphenyl ether to about 12-48 moles of liquid bromine containing a catalytic amount of a zirconium halide at a temperature from ambient up to reflux.

10. A process of claim 1 further characterized by including a small promoter amount of iron together with said zirconium halide catalyst.

11. A process of claim 10 further characterized by using about 6-24 moles of bromine for each equivalent weight of said polyphenylene ether wherein said equivalent weight is the molecular weight of the polyphenylene ether divided by the number of benzene rings in said polyphenylene ether.

12. A process of claim 11 wherein said polyphenylene ether is diphenyl ether.

13. A process of claim 12 wherein said iron promoter is added in the form of iron particles.

14. A process of claim 13 conducted using about 12-48 moles of bromine per mole of diphenyl ether.

15. A process of claim 14 wherein said diphenyl ether is added to the bromine containing the zirconium halide catalyst and iron promoter.

16. A process of claim 15 wherein said zirconium halide catalyst is added to the bromine in the form of zirconium chloride.

17. A process for making brominated diphenyl ether which contains an average of about 6-8 bromine atoms per molecule, said process comprising adding about 1 mole of molten diphenyl ether to about 12-48 moles of liquid bromine containing a catalytic amount of a zirconium halide catalyst and a promoter amount of iron at a temperature from ambient up to reflux.

* * * * *

UNITED STATES PATENT AND TRADEMARK OFFICE
CERTIFICATE OF CORRECTION

PATENT NO.  : 4,717,776
DATED       : January 5, 1988
INVENTOR(S) : David R. Brackenridge, et al.

It is certified that error appears in the above-identified patent and that said Letters Patent is hereby corrected as shown below:

Abstract, line 2, reads "diphenly" and should read -- diphenyl --.

Column 1, line 20, reads "referred to at" and should read -- referred to as --.

Column 1, line 22, reads "dipheny" and should read -- diphenyl --.

Column 3, line 15, reads "operation of the" and should read -- operation the --.

Column 3, line 67, reads "layer separated" and should read -- layer was separated --.

Column 6, line 12, reads "process fo" and should read -- process of --.

Signed and Sealed this

Seventh Day of June, 1988

Attest:

DONALD J. QUIGG

*Attesting Officer*   *Commissioner of Patents and Trademarks*